United States Patent [19]

Klaus et al.

[11] Patent Number: 4,604,059
[45] Date of Patent: Aug. 5, 1986

[54] DENTAL COMPOSITIONS, FIRED DENTAL PORCELAINS AND PROCESSES FOR MAKING AND USING SAME

[75] Inventors: Irving Klaus, Santurce; Warren Herbstman, Isla Verde; Jairo Lopez, La Riviera, all of P.R.

[73] Assignee: Excelco International, Inc., Santurce, P.R.

[21] Appl. No.: 688,746

[22] Filed: Jan. 4, 1985

[51] Int. Cl.$^4$ ................................................. A61C 5/00
[52] U.S. Cl. .................................... 433/217.1; 106/35; 433/199.1; 433/201.1; 433/218; 433/222.1; 433/226; 433/228.1
[58] Field of Search ................. 106/35; 433/212, 218, 433/222, 199, 201, 226, 228, 217

[56] References Cited

U.S. PATENT DOCUMENTS

| | | | |
|---|---|---|---|
| 3,423,829 | 1/1969 | Halpern et al. | 106/35 |
| 3,488,847 | 1/1970 | Pettrow | 433/212 |
| 4,321,042 | 3/1982 | Scheicher | 106/35 |
| 4,431,451 | 2/1984 | Mabie et al. | 106/35 |
| 4,455,383 | 6/1984 | Panzera | 106/35 |
| 4,473,353 | 9/1984 | Greggs | 433/215 |
| 4,475,892 | 10/1984 | Faunce | 106/35 |

*Primary Examiner*—Lorenzo B. Hayes
*Attorney, Agent, or Firm*—Lerner, David, Littenberg, Krumholz & Mentlik

[57] ABSTRACT

A composition for making a fired dental porcelain is disclosed which composition comprises a powder dental porcelain frit material and a second material. The second material is selectively etchable from a fired dental porcelain prepared from the composition and the second material can, upon such firing of the composition, maintain a separate phase so that, when the composition is formed into a fired dental porcelain having a dental porcelain surface to be bonded to a dental substrate and the dental porcelain surface is etched to remove second material therefrom, the porosity and surface area of the dental porcelain surface will be increased to provide enhanced bonding of the dental porcelain surface to the dental substrate. Also disclosed are fired dental porcelains prepared therefrom and methods of making and using same.

20 Claims, No Drawings

DENTAL COMPOSITIONS, FIRED DENTAL PORCELAINS AND PROCESSES FOR MAKING AND USING SAME

BACKGROUND OF THE INVENTION

The present invention relates to compositions for making fired dental porcelains, to fired dental porcelains themselves, and to processes for making and using fired dental procelains. More particularly, the present invention relates to dental compositions, fired dental procelains and processes providing enhanced bonding of a dental porcelain to a surface of a dental substrate, e.g., the surface of a tooth.

Various techniques and compositions have been used to prepare fired dental porcelains in predetermined shapes for use as, e.g., porcelain veneers, inlays, crowns, dentures and other dental constructions. For example, in an article by Robert Nixon entitled "Use of Porcelain Laminate Veneers Enhances Foreshortened, Worn Teeth," Dentistry Today, October, 1984, pp. 27-31, a general technique of preparing porcelain veneers is discussed. As pointed out in this article, after the porcelain veneers have been formed, baked and glazed, the inner surface of the veneers (i.e., the surface to be attached to the tooth) is etched with a strong acid, usually hydrofluoric acid. While this general technique has provided most times adequate veneer bonding, one drawback of the technique is that the bond between the tooth surface and the etched surface of the porcelain veneer is not always strong. Thus, it would be desirable to be able to provide a stronger bond between the inner veneer surface and the tooth surface (or for that matter the surface of any porcelain to be attached to the surface of a dental substrate).

Another method for making a veneer from a porcelain dental frit material is disclosed in Greggs U.S. Pat. No. 4,473,353. Similar to the general technique discussed in the above paragraph, the Greggs patent in Column 3, lines 62-64 mentions that the inside surface of the veneer can be etched, usually by air abrasion, to promote bonding thereof to the enamel tooth surface.

A laminated veneer is disclosed in Faunce U.S. Pat. No. 4,475,892 in which the veneer is made up of, usually, three laminated layers with each layer including a plurality of elongated vitreous microsized ceramic rods. In connection with FIGS. 7 and 8 of this patent, it is disclosed that the ceramic material may also incorporate combinations of acid soluble glass fibers together with acid resistant glass fibers, with the former being acid etchable. See, for example, Column 5, lines 44-65 of the patent. Such multi-layer veneers, however, have a number of distinct disadvantages, e.g., they are complex in structure and relatively difficult to make. They require relatively highly skilled technicians or even experts to construct them properly. In the dental field, it is highly desirable that veneers and other dental constructions can be made quickly and simple by ordinary technicians so that the cost and time involved for the patient can be minimized. Such laminated veneers as disclosed in the Faunce patent do not provide such desirable characteristics.

Etching has also been used for other purposes in other non-analogous arts, e.g., in the integrated circuit art. See, for example, U.S. Pat. No. 3,650,960. Also, other disclosures have been made in connection with solutions for etching dental porcelain. See, for example, Cheung U.S. Pat. No. 4,376,673.

SUMMARY OF THE INVENTION

It has now been found that a fired dental porcelain providing enhanced bonding of the dental porcelain to the surface of a dental substrate can be provided by a composition comprising a powder dental porcelain frit material and a second material, which is selectively etchable from a fired dental porcelain prepared from the composition. The second material can, upon firing of the composition, maintain a separate phase so that, when the composition is formed into a fired dental porcelain having a dental porcelain surface to be bonded to a surface of a tooth and the dental porcelain surface is etched to remove second material therefrom, the porosity of the dental porcelain surface will be increased to provide enhanced bonding of the dental porcelain surface to the surface of the tooth. Thus, the fired and etched composition provides a highly desirable fired dental porcelain. The inclusion of the second material, e.g., free silica or any other material which is selectively etchable from a fired dental porcelain, in the composition even in small amounts has been found to materially increase bondability of the fired and etched dental porcelain to dental substrates such as a tooth surface. Moreover, the composition of the invention is relatively simple and quick to prepare for use and does not require highly skilled technicians or experts.

The invention also involves a process for making a fired and etched dental porcelain for bonding to a dental substrate in which a dental porcelain composition is provided comprising a powdered dental porcelain frit material and a second material as described above. The dental porcelain composition is formed into a predetermined shape having a dental porcelain surface for attachment to a dental surface. The dental porcelain composition in its predetermined shape is fired so as to provide a fired dental porcelain in which the second material is maintained as a separate phase. The dental porcelain surface of the fired dental porcelain is etched with an etching material which selectively removes the second material from the dental porcelain surface to increase the porosity of such dental porcelain surface so as to provide enhanced bonding of the dental porcelain surface to the dental substrate.

The invention further involves a process for tooth repair comprising the steps of providing a fired dental porcelain comprising a fired dental porcelain composition as described above, wherein said fired dental porcelain has a dental porcelain surface shaped to be bonded to a surface of a tooth to be repaired and said dental porcelain surface is etched to remove second material therefrom to increase the porosity of said dental porcelain surface and thereby provide enhanced bonding of said dental porcelain surface to such a surface of a tooth; and bonding said etched dental porcelain surface to a surface of a tooth to be repaired.

DETAILED DESCRIPTION OF THE INVENTION

The composition of the present invention includes a powder dental porcelain frit material as is conventional in the art for preparing fired dental porcelain. Conventional dental porcelain frits presently are prepared from crystalline oxides such as feldspar, quartz, boric oxide and the like. Any of such conventional powder dental porcelain frit materials can be employed in the present invention. Suitable powder dental porcelain frit materials include those described in Weinstein et al. U.S. Pat. No. 3,052,982, the disclosure of which is incorporated herein for its description of dental porcelain frit materials and their method of preparation. In general, the powder dental porcelain frit materials are prepared by firing a mixture of the desired crystalline oxides (or the precursers thereof which provide the oxides upon firing, e.g., lithium carbonate) until the mixture is in a vitreous state. The mixture is thereafter cooled and powdered to an appropriate size as is conventional in the art. Combinations of such frits can also comprise the powder dental porcelain frit material for use in the present invention. Other suitable powder dental porcelain frit materials include, for example, those disclosed in U.S. Pat. No. 4,455,383 and commercially available materials.

The powder dental porcelain frit material for use in the present invention can, for example, comprise feldspar, e.g., soda or potash, and at least one of glass, kaolin, silica, boric oxide and mixtures thereof. Fluxing agents can be employed to provide desired expansion characteristics, e.g., as discussed in the Weinstein et al. patent. A preferred powder dental porcelain frit material comprises potassium feldspar, glass and lithium carbonate, which mixture has been fired, cooled and powdered in a conventional manner to provide the powder dental porcelain frit material. Preferably, such material includes a combination of frit materials. One of the frit materials includes from about 85 to about 98% by weight of potassium feldspar, from about 2 to about 15% by weight of the lithium carbonate or other lithium oxide precurser. The other frit material includes from about 30 to about 70% by weight potassium feldspar, and from about 70 to about 30% by weight of glass. These two frit materials can be used in a weight ratio of from 70:30 to 30:70 in forming the powder porcelain dental frit material for use in the present invention.

The powder dental porcelain frit material employed in the present invention can also include other materials therein as is conventional in the art. For example, the powder dental porcelain frit material can include pigments, opaquing agents, binders, fluxing agents and mixtures of such materials. Suitable pigments include the conventional ceramic coloring pigments used in the ceramic industry, while suitable opaquing agents include tin oxide, zirconium oxide, zirconium silicate and titanium dioxide. Although a binder is not necessary, a suitable binder for such composition would be one which upon firing is removed from the fired dental porcelain, e.g., water. Suitable fluxing agents include, for example, lithium oxide, sodium oxide, potassium oxide, strontium oxide, calcium oxide, magnesium oxide, precursers of such oxides and mixtures thereof, e.g., lithium carbonate. These additives are included in the composition in an amount effective to achieve the purpose of such additive as is conventional in the art.

Typically, the powder dental porcelain frit material passes through a 165 mesh screen giving an average particle size in a range of from about 0.01 microns to about 88 microns. Also, the powder dental porcelain frit material is included in the composition in an amount of from about 95 to about 99.99% by weight. On a macroscale, the powder dental porcelain frit material, because it is pre-reacted, is relatively homogeneous in composition, while on a microscale, there are areas containing crystalline materials, in various degrees of digestion.

The composition of the present invention also includes a second material. This second material is selectively etchable from a fired dental porcelain prepared from the composition. The second material also maintains a separate phase upon firing of the composition to provide such a dental porcelain. This separate phase is provided because the second material on a macroscale is different compositionally from the powder dental porcelain frit material. Thus, when the dental porcelain is prepared from the fired composition, the firing does not cause all or even most of the second material to become part of the integrated structure of the fired dental porcelain. Rather, although some of the second material becomes fused on the outer surface of the particles to the dental porcelain fritted material in the fired dental porcelain, a good portion of the second material remains as a separate phase within the fired dental porcelain structure. Accordingly, the dental porcelain surface to be bonded to a dental substrate can be etched to remove the second material therefrom and increase the porosity of the dental porcelain surface. By this means, an enhanced bonding of the dental porcelain surface to the dental substrate is provided.

Suitable materials for use as the second material in the composition of the invention include, for example, free silica, vitreous silica, fused silica, flint, fumed silica, quartz, $CaSiF_4 \cdot 2H_2O$, $Si_2N_4$, leschatelierite, tridymite, natural opal, $ZrO_2$, $ZrSiO_4$, and mixtures thereof. A preferred etchable material is flint.

The second material can be etchable by any suitable means, depending upon the second material itself. For example, acid etchable or air-abrasion etchable materials can be employed. Preferably, the etchable material is a hydrofluoric acid etchable material.

The second material in the composition of the present material is present in an amount to provide a sufficient proportion of the second material at the dental porcelain surface to provide the desired porosity of such surface to enhance bonding of the dental porcelain surface to a dental surface. Suitably, the second material is included in the composition of the present invention in an amount of from about 0.01 to about 5% by weight. The preferably from about 0.15 to about 0.5% by weight. The second material preferably has an average particle size in the range of from about 0.01 microns to about 300 microns, e.g., the material which passes through a 50 mesh screen, preferably through a 200 mesh screen.

To prepare the composition of the present invention, the powder dental porcelain frit material, e.g., combination of frits, is physically mixed with the second material. This can be done, for example, by ball milling, blending in a blender, e.g., a V-cone blender, etc.

The composition of the invention can be employed in the same manner as a powder dental porcelain frit material itself, since the second material is not included in an amount sufficient to alter the ability of the composition to produce a suitable fired dental porcelain. Preparation of dental porcelains for bonding to the surface of a tooth or for bonding to other dental constructions such as denture bases, etc. are well-known in the art and need not be detailed here. Thus, the composition of the invention can be used in preparing dentures, dental veneers, jacket-crowns, inlays and constructions over metal or with alumina substrates, etc. in the conventional processes for preparing such constructions. In general, the powder dental porcelain frit material is prepared into the desired shape of the denture, veneer, etc. by techniques well-known in the art and as briefly described below. The composition is then fired in its predetermined shape to provide a fired dental porcelain having the desired shape. The surface of the fired dental porcelain to be bonded to the tooth, denture substrate, etc. is then etched, for example, with an etching material which will remove at least some of the second material from such surface of the fired dental porcelain. This removal of the second material provides "pits" or increased porosity and surface area on the surface of the fired dental porcelain to be bonded. Thus, when such surface is then bonded to the dental substrate, the increased porosity provides a firmer bond between the fired dental porcelain and substrate because the bonding agent is able to form a better physical hold on the surface and provide a greater physical retention.

The composition of the invention can be formed into the desired predetermined shape by any of the techniques conventional in the art for preparing the desired end product, i.e., a denture, veneer, an inlay, etc. In general, an impression is made of the substrate, e.g., a tooth. The impression is used to make a model with which the ultimate fired dental porcelain is prepared. By dental substrate, we mean the surface of a tooth, e.g., for a veneer, inlay or onlay, the metal coping of a crown, or a denture base, e.g., acrylics, to which the fired dental porcelain will be bonded.

In a preferred embodiment of the invention, the composition of the invention and the fired dental porcelain of the invention is prepared into porcelain veneers. Techniques for preparing such dental porcelain veneers are disclosed, for example, in the Nixon article discussed above and in Greggs U.S. Pat. No. 4,473,353, the disclosures of which are incorporated herein by reference for their teachings in connection with techniques for preparing veneers from porcelain frit materials. Preferably, the composition of the invention is used to prepare veneers by the process generally described in the Greggs patent. However, the composition of the invention can be used with any of the techniques disclosed in the art for preparing such veneers, etc., since the composition of the invention functions primarily as a conventional powder dental porcelain frit material, except for the fact that it has the desirable properties provided the second material as discussed in detail above.

Another popular method for fabricating porcelain veneers, inlays or porcelain jacket-crowns is to fire the procelain frit material on or into a refractory model to form the desire veneer, inlay, or porcelain jacket-crown thereon. After removing the refractory model, the fired dental porcelain produced is etched as described above.

Once the powder dental porcelain frit material is in its predetermined and desired shape, it is fired as is conventional for preparation of the various dental porcelain constructions in the art. The composition in its predetermined shape is fired at a temperature and for a time so that the powder dental porcelain frit material fuses together as is conventional in the art for preparation of a fired dental porcelain, but so that the second material maintains separate phases within the fired dental porcelain structure. Thus, while some of the second material may fuse to the powder dental porcelain frit material during firing, relatively large portions of the second material remain as such in the fired dental porcelain, i.e., the second material does not become part of a homogeneous fired dental porcelain on a macroscale. Rather, relatively large particles of the second material remain as such in the fired dental porcelain. Typically, the composition of the invention is fired at a temperature of from about 600° C. to about 1200° C. Since the dental porcelain frit particles which are relatively compositionally homogeneous on a macroscale because of their previous fusion, calcination and powdering, they quickly form a conventional dental porcelain structure upon firing without integrating the second material therein as a part of a homogeneous structure. Thus, the composition of the invention can normally be fired at the temperatures and for the times recommended for the particular powder dental porcelain frit material employed, since under such conditions the second material will not become part of the dental porcelain structure.

Once the composition has been fired, a dental porcelain in the predetermined shape is provided, i.e., in the shape of a veneer, denture, inlay, etc. as discussed above. The surface of the dental porcelain to be attached to the dental substrate is etched to remove second material from such dental porcelain surface, to increase the porosity of that surface and thereby to enhance the bondability of that dental porcelain surface to the desired substrate. The etching technique employed depends upon the nature of the second material included in the composition of the invention. Typically, an acid etchable and preferably a hydrofluoric acid etchable second material is employed. However, second materials which could be etched from the fired dental porcelain by other etching techniques such as air abrasion can also be employed. The only requirement is that the second material be etchable and that it not affect the ability of the powder dental porcelain frit material to provide a good quality fired dental porcelain.

As noted above, the second material is preferably a fluoride etchable material which is preferentially etched from the fired dental porcelain. Suitable etching compositions include dilute hydrofluoric acid solutions or gells. For example, Cheung U.S. Pat. No. 4,476,673 discloses an etching gell composition. The time which the etching material is allowed to remain in contact with the dental porcelain surface varies depending upon the nature of the second material and the strength of, for example, the hydrofluoric acid composition employed.

The fired dental porcelain in its predetermined shape is then bonded to the dental substrate by techniques conventional in the art. For example, with a porcelain veneer, the etched surface of the porcelain veneer and the acid etched enamel surface of a tooth (which can be reduced so as to decrease the bulk resulting from the addition of the veneer) can be first treated by applying a silane bonding agent on both surfaces. A composite luting agent can then be used to provide the bond between the etched surfaces in a manner which is conventional in the art, see, for example, the Nixon article and Greggs patent cited above.

In a preferred embodiment of the invention, the composition and fired dental porcelain of the present invention are used to prepare veneers for application to labial surfaces of teeth in accordance with techniques as disclosed in the Nixon article cited above and the process of the Greggs U.S. Pat. No. 4,473,353. By employing the composition and fired dental porcelain of the present invention in making such veneers, a better bond to the tooth surface is provided with its attendant advantages.

The following example is intended to illustrate, but not to limit, the present invention.

EXAMPLE

A first powder porcelain frit material was prepared by mixing feldspar and lithium carbonate at about 94% by weight feldspar to about 6% by weight lithium carbonate. A second powder dental porcelain frit material was prepared by mixing about 50% by weight feldspar and about 50% by weight glass. These two mixtures were individually pre-reacted by firing and then ground. The frit materials were screened to provide the desired particle size. In this case, 165 mesh screen was employed. The two fritted materials were then mixed in a ratio of about 50:50. It must be noted that the exact proportions of the individual ingredients must be adjusted depending upon the nature of the feldspar employed as discussed in the Weinstein et al. patent to provide the desired expansion characteristics, since feldspar composition varies because it is a natural material.

The frits were blended together to make a dental porcelain and colored with ceramic pigments to match a specific shade guide. To this blended mixture was added 200 mesh flint in an amount of about 0.25% by weight of the total composition.

The above described composition was used to prepare a veneer in accordance with the method as described in the Greggs patent cited above. The resultant fired porcelain in the form of a veneer was etched with hydrofluoric acid gel (applied for about 8 minutes) on the surface of the veneer to be bonded to a tooth. In comparison to conventionally etched porcelain veneers not having the second material as in the present invention similarly prepared by the same method as described in the Greggs patent, the veneers prepared with the composition of the present invention provided a much firmer bond to the tooth substrate.

It will be understood that the embodiments described above are merely exemplary and that persons skilled in the art may make many variations and modifications without departing from the spirit and scope of the invention. All such modifications and variations are intended to be included within the scope of the invention as defined by the appended claims.

What is claimed is:

1. A process for making a fired, etched dental porcelain for bonding to a dental substrate, said process comprising the steps of providing a dental porcelain composition comprised of a powder dental porcelain frit material and a second material which is selectively chemically etchable from a fired dental porcelain prepared from the composition and which, upon firing of the composition, maintains a separate phase with respect to said powder dental porcelain frit material; forming said dental porcelain composition into a predetermined shape having a dental porcelain surface for attachment to a dental substrate; firing the dental porcelain composition in the predetermined shape so that the second material in the composition is maintained in the fired dental porcelain as said separate phase; and chemically etching said dental porcelain surface with a chemical etching material which selectively removes said second material from said dental porcelain surface to increase the porosity of such dental porcelain surface so as to provide enhanced bonding of said dental porcelain surface to a dental substrate.

2. A process according to claim 1, wherein said powder dental porcelain frit material comprises feldspar and at least one of glass, kaolin, silica, boric oxide or mixtures thereof.

3. A process according to claim 1, wherein said powder dental porcelain includes at least one additive selected from the group consisting of pigment, opaquing agent, binder, fluxing agent, and mixtures thereof.

4. A process according to claim 3, wherein the fluxing agent is selected from the group consisting of lithium oxide, sodium oxide, potassium oxide, strontium oxide, calcium oxide, magnesium oxide, precursers of such oxides and mixtures thereof.

5. A process according to claim 1, wherein said powder dental porcelain frit material comprises potassium feldspar, glass, and lithium carbonate which has been fired, cooled and powdered.

6. A process according to claim 1, wherein said second material comprises an etchable material selected from the group consisting of flint, vitreous silica, fused silica, fumed silica, quartz, $CaSiF_4 \cdot 2H_2O$, tridymite, natural opal, $ZrO_2$, $ZrSiO_4$, and mixtures thereof.

7. A process according to claim 1, wherein said second material has an average particle size in the range of from about 0.1 microns to about 200 microns.

8. A process according to claim 1, wherein said second material is present in said composition in an amount of from about 0.01 to about 5% by weight.

9. A process according to claim 1, wherein said second material is a hydrofluoric acid etchable material and said dental porcelain surface is etched with a hydrofluoric acid containing composition.

10. A process according to claim 1, wherein the composition is fired in the form of a dental veneer, inlay, crown, denture or jacket.

11. A process for tooth repair comprising the steps of providing a fired dental porcelain comprising a fired composition including a powder dental porcelain frit material and a second material which is selectively chemically etchable from said fired dental porcelain and which maintains a separate phase with respect to said powder dental porcelain frit material upon such firing, wherein said fired dental porcelain has a dental porcelain surface shaped to be bonded to a surface of a tooth to be repaired and said dental porcelain surface is chemically etched with a chemical etching material to remove second material therefrom to increase the porosity of said dental porcelain surface and thereby provide enhanced bonding of said dental porcelain surface to such a surface of a tooth; and bonding said etched dental porcelain surface of the fired dental porcelain to a surface of a tooth to be repaired.

12. A process according to claim 11, wherein said powder dental porcelain frit material comprises feldspar and at least one of glass, kaolin, silica, boric oxide or mixtures thereof.

13. A process according to claim 11, wherein said powder dental porcelain includes at least one additive selected from the group consisting of pigment, opaquing agent, binder, fluxing agent, and mixtures thereof.

14. A process according to claim 13, wherein the fluxing agent is selected from the group consisting of lithium oxide, sodium oxide, potassium oxide, strontium oxide, calcium oxide, magnesium oxide, precursers of such oxides and mixtures thereof.

15. A process according to claim 11, wherein said powder dental porcelain frit material comprises potassium feldspar, glass, and lithium carbonate which has been fired, cooled and powdered.

16. A process according to claim 11, wherein said second material comprises an etchable material selected from the group consisting of flint, vitreous silica, fused silica, fumed silica, quartz, $CaSiF_4.2H_2O$, tridymite, natural opal, $ZrO_2$, $ZrSiO_4$, and mixtures thereof.

17. A process according to claim 11, wherein said second material has an average particle size in the range of from about 0.1 microns to about 200 microns.

18. A process according to claim 11, wherein said second material is present in said composition in an amount of from about 0.01 to about 5% by weight.

19. A process according to claim 11, wherein said second material is a hydrofluoric acid etchable material and said dental porcelain surface is etched with a hydrofluoric acid containing composition.

20. A process according to claim 11, wherein the fired dental porcelain is in the form of dental veneer, inlay, crown or jacket.

* * * * *

UNITED STATES PATENT AND TRADEMARK OFFICE
CERTIFICATE OF CORRECTION

PATENT NO. : 4,604,059

DATED : August 5, 1986

INVENTOR(S) : Irving Klaus, et al.

It is certified that error appears in the above-identified patent and that said Letters Patent is hereby corrected as shown below:

Column 8, line 23, "0.1" should read --0.01-- and
          line 23, "200" should read --300--.

Column 9, line 8, "0.1" should read --0.01-- and
          line 8, "200" should read --300--.

Signed and Sealed this

Thirteenth Day of January, 1987

Attest:

DONALD J. QUIGG

Attesting Officer

Commissioner of Patents and Trademarks